(12) United States Patent
Cheung et al.

(10) Patent No.: US 8,048,372 B1
(45) Date of Patent: Nov. 1, 2011

(54) SENSOR SYSTEM FOR REAL-TIME BIOLUMINESCENCE SIGNATURE DETERMINATION

(75) Inventors: Ken C. K. Cheung, Kailua, HI (US); Ronald L. Seiple, Kailua, HI (US); Christopher J. Sullivan, Honolulu, HI (US); Paul Pernambuco-Wise, Fairfax, CA (US); Randy Wolfshagen, Koloa, HI (US); S. Maile Giffin, Honolulu, HI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 802 days.

(21) Appl. No.: 11/500,268

(22) Filed: Aug. 7, 2006

Related U.S. Application Data

(60) Provisional application No. 60/705,813, filed on Aug. 5, 2005.

(51) Int. Cl.
*G01N 21/76* (2006.01)
(52) U.S. Cl. ....... 422/52; 250/573; 250/239; 250/559.1; 356/28; 356/213; 356/427; 435/286.7; 435/288.7; 73/61.51; 73/170.29; 367/131

(58) Field of Classification Search ............... 73/170.29, 73/170.33; 702/2, 5, 3; 367/131; 348/81
See application file for complete search history.

(56) References Cited

U.S. PATENT DOCUMENTS

| | | | | |
|---|---|---|---|---|
| 5,264,906 A | * | 11/1993 | Ferer et al. ...................... 356/28 |
| 6,536,272 B1 | * | 3/2003 | Houston et al. ............ 73/170.29 |
| 6,570,176 B1 | * | 5/2003 | Fucile ........................... 250/573 |
| 7,040,157 B2 | * | 5/2006 | Glasgow et al. ........... 73/170.29 |

* cited by examiner

*Primary Examiner* — Sally Sakelaris
(74) *Attorney, Agent, or Firm* — James Creighton Wray

(57) ABSTRACT

A real-time in-situ sensor system is provided for measurement of bioluminescence and determination of bioluminescence surface signature. The system measures bioluminescence in the wake of a submerged moving object as well as ambient light levels outside of the wake. Along with measurements of depth and water-quality parameters including turbidity, temperature and salinity, the surface signature of the induced underwater bioluminescence can be calculated by considering light transmission and attenuation through water. With this real-time information, the operator of the submerged moving object can employ tactical maneuvers to affect the resultant surface signature.

23 Claims, 4 Drawing Sheets

Conceptual rendering of invention implemented on a submersible

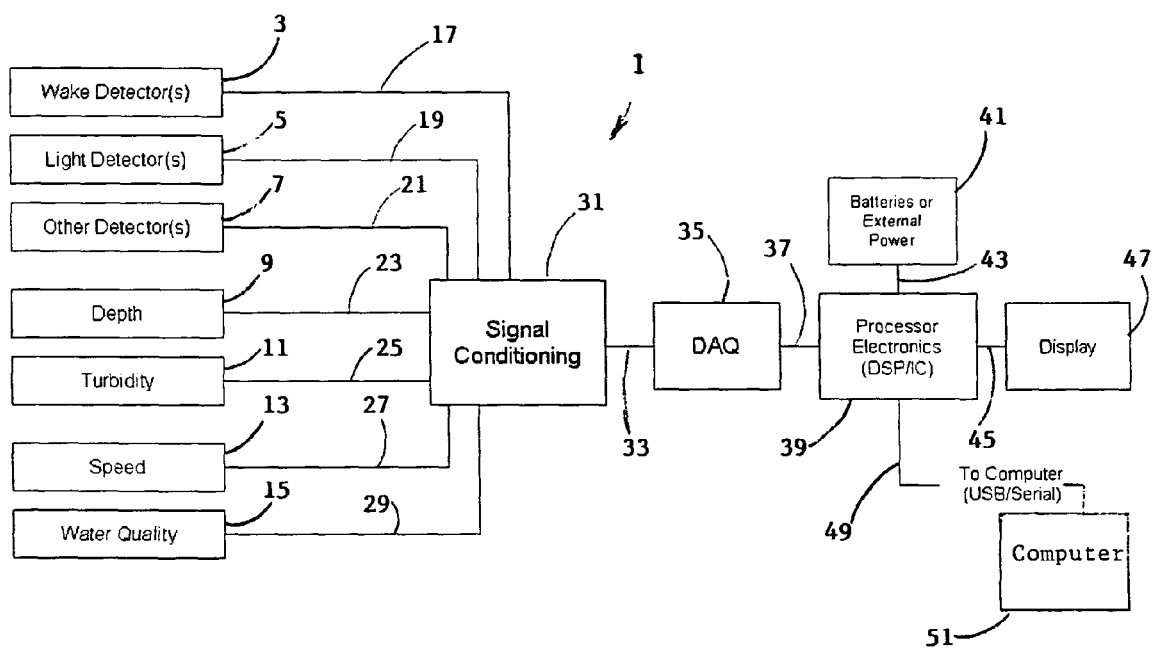
FIGURE 1  Components of Sensor System

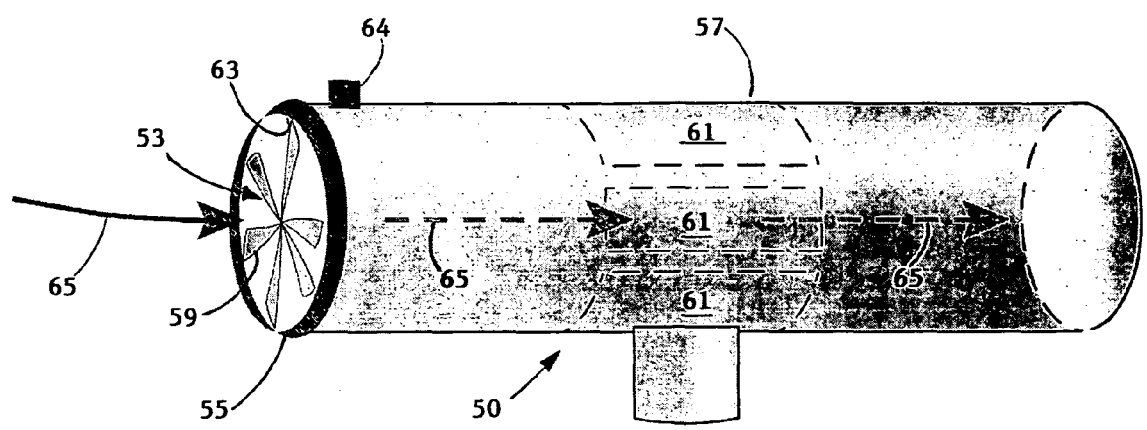
FIGURE 2 Flow-Through Tube Bioluminescence Detector

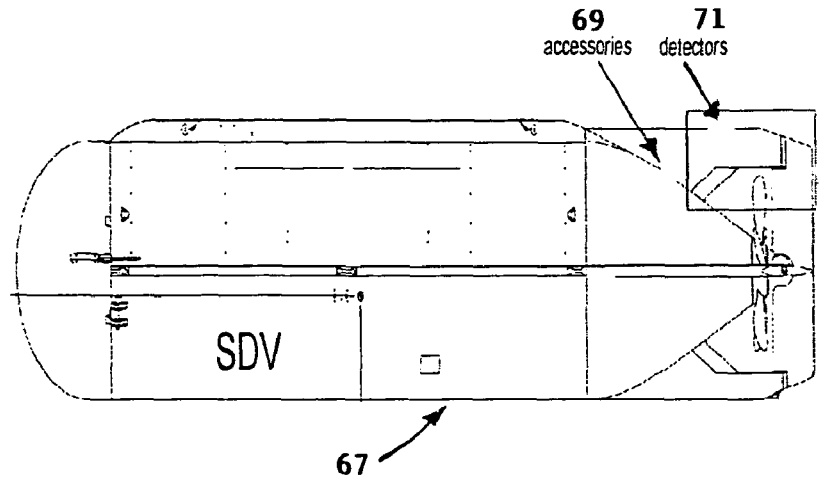
FIGURE 3A    Example of placement of detectors and accessories (batteries, circuitry, transmissometer, depth gauge, other sensors) on submersible.
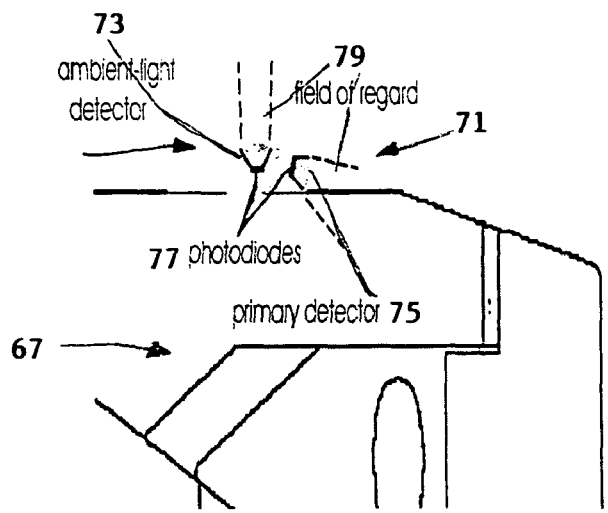
FIGURE 3B    Detector concept details

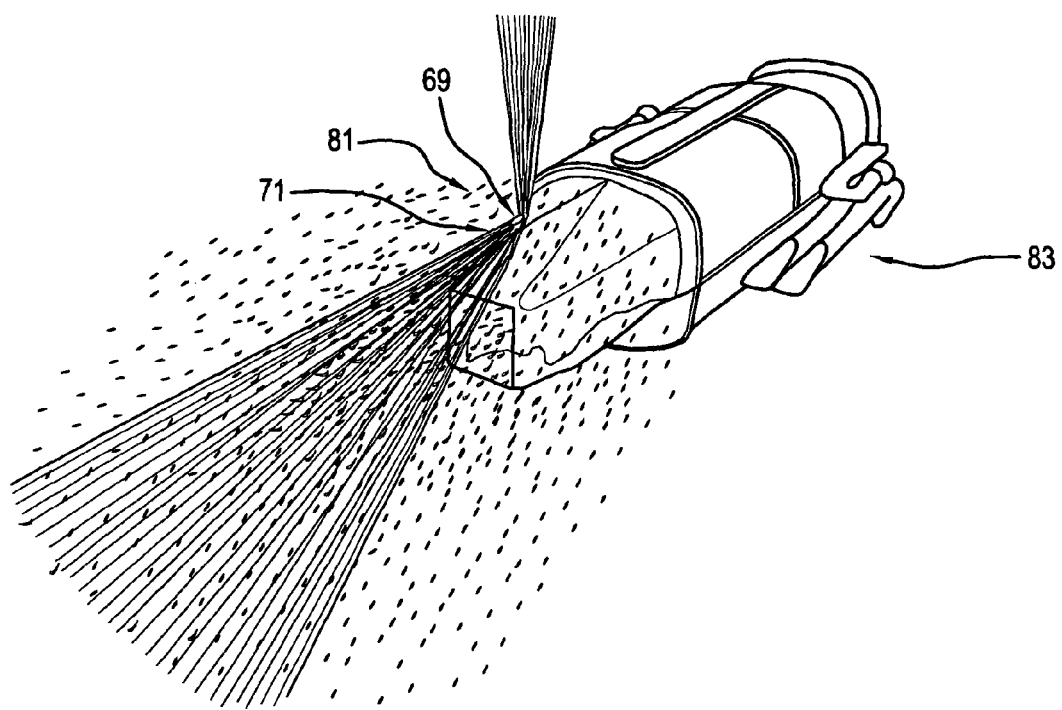
FIGURE 4  Conceptual rendering of invention implemented on a submersible

SENSOR SYSTEM FOR REAL-TIME BIOLUMINESCENCE SIGNATURE DETERMINATION

This application claims the benefit of U.S. Provisional Application No. 60/705,813, filed Aug. 5, 2005, which is hereby incorporated by reference in its entirety.

FIELD OF THE INVENTION

This invention relates to optical sensing of the underwater environment, specifically bioluminescence signature created by moving submerged objects such as submersibles, swimmers and watercraft, and its observability from the surface.

BACKGROUND OF THE INVENTION

Bioluminescence is a localized phenomenon caused when organisms are stimulated by flow agitation. As a result of this effect, submerged moving objects will be highlighted with a blue-green glow and often can produce spectacular glowing wakes from ships and submerged craft. This effect is so widespread in the world's coastal regions that some level of bioluminescence is almost always present. Dinoflagellates, ubiquitous unicellular plankton also known for producing harmful blooms, are the most common sources of bioluminescence in the littoral zone. Dinoflagellates often exist in sufficient density such that ships, swimmers and submersibles can readily be detected by airborne, seaborne, or land-based observers. The intensity of bioluminescence is dependent on the local abundance of the dinoflagellates, which varies both in space and time. This makes the phenomenon difficult to predict, and when bioluminescent organisms are present, it is unavoidable by any practical means.

Ships, submarines and swimmers can readily be detected in the dark when strong bioluminescence activity exists, which poses a serious problem when movements need to be hidden from detection. When bioluminescence is present, there are ways to minimize the amount of signature that is detectable from the surface. In the case of submersibles and swimmers, detection vulnerability can be reduced by either decreasing the amount of flow stimulation caused by the craft (e.g., reducing speed) or by increasing operating depth, thus attenuating the surface signature caused by bioluminescence. The problem is that the operator must know in real time the bioluminescence intensity generated by the submersible's movement and how this is translated to surface signature and ultimately the vulnerability to detection. The operator must also know to what extent tactical maneuvers are effective in changing the bioluminescence signature at the surface.

Currently, this real-time self-monitoring capability does not exist.

Needs exist for a real-time, self-monitoring bioluminescence signature determination sensor.

SUMMARY OF THE INVENTION

The invention is a real-time in-situ bioluminescence detector for tactical use on submersible craft and swimmers. The miniature device can automatically provide continuous vulnerability assessment information to the vehicle operator or swimmer.

With this real-time quantifiable bioluminescence signature output, such a device could then recommend tactical procedures to reduce this signature by several means, for example, increasing depth, decreasing speed, combinations thereof, or any other similar evasive tactics.

This real-time in-situ device provides a way for operators to assess how far they can be seen based on nighttime luminescence and ambient light. It then allows the operators to modify their movement and/or change their locations continuously in response to the continuous real-time feedback they get from the device.

The invention provides a bioluminescence sensor for measurement of bioluminescence, for determination of bioluminescence surface signature, and for providing real-time information of the bioluminescence and the bioluminescence surface signature to the operator of a submerged moving object. The bioluminescence sensor of the invention includes one or more photodetectors, one or more ambient light detectors, one or more detectors used to measure sampled water characteristics in an enclosed space, a depth gauge, a device to measure turbidity, a speed indicator, a temperature measurement device, a pH measurement device, a salinity measurement device, a signal conditioning stage, a data acquisition system, a processor, an output, and a power source. The bioluminescence sensor further includes a dissolved oxygen measurement device.

The photodetectors of the bioluminescence sensor may be photodiodes, avalanche photodiodes (APD), photomultipliers, balanced photoreceivers, spectrometers, or similar photodetectors. The sensor's device to measure turbidity may be a light transmissometer, turbidity meter, or similar device to determine the effect or suspended solids in the water on light transmission. The sensor's speed indicator may be an anemometer or other similar device to measure velocity. The temperature measurement device of the bioluminescence sensor may be a thermistor, thermometer, or other similar instrument. The power source of the invention is either that of an external power source or a battery.

The signal conditioning stage of the invention further includes filters, pre-amplifiers, and amplifiers, and the processor consists of a digital signal processor (DSP), integrated circuit, field programmable gate array (FPGA), embedded system or other similar device.

The output system of the invention is a display and/or a computing device.

A new method of real-time bioluminescence sensing provides an apparatus including one or more photodetectors, one or more ambient light detectors, one or more detectors used to measure sampled water volumes in an enclosed space, a depth gauge, a device to measure turbidity, a speed indicator, a temperature measurement device, a pH measurement device, a salinity measurement device, a signal conditioning stage, a data acquisition system, a processor, an output system and a power source. That apparatus is then used to sense the bioluminescence signature of a body in water.

The apparatus of the new method of real-time bioluminescence sensing is powered by the power source. Information is then collected from the one or more photodetectors, the one or more ambient light detectors, the one or more detectors used to measure sampled water volumes in an enclosed space, the depth gauge, the device to measure turbidity, the speed indicator, the temperature measurement device, the pH measurement device, and the salinity measurement device. That collected information is passed to the signal conditioning stage where it is conditioned and passed from the conditioning stage to the data acquisition system. Information is acquired from the conditioned data, and the acquired information is passed to the processor. The acquired information is processed in the processor to determine the bioluminescence signature of the body.

The new method further includes predicting the potential bioluminescence signature of the body based upon changes in movement, speed, position, or other characteristics desired by the user.

The results of the processor are sent to a display and/or another computing device.

These and further and other objects and features of the invention are apparent in the disclosure, which includes the above and ongoing written specification, with the drawings.

BRIEF DESCRIPTION OF THE DRAWINGS

FIG. 1 is a block diagram of the sensor system.

FIG. 2 shows details of the flow-through tube measurement detector.

FIGS. 3A and 3B show examples of a system implemented onto the tail assembly of a submersible (Seal Delivery Vehicle or SDV).

FIG. 4 shows the sensor system used on a submersible.

DETAILED DESCRIPTION OF THE PREFERRED EMBODIMENTS

FIG. 1 shows a block diagram of various components of the system 1. One or more detectors 3 including photodiodes, avalanche photodiodes (APD), photomultipliers, balanced photoreceivers, spectrometers, or similar photodetectors are used to measure the light intensity in the wake of the object. One or more ambient light detectors 5 are used to measure light levels outside of the wake. Other detectors 7 can be used to measure sampled water volumes in an enclosed space (FIG. 2). A depth gauge 9 is used to measure the operating depth of the sensor system. A turbidity measurement is performed by a device 11, for example a light transmissometer, turbidity meter or similar device to determine the effect of suspended solids in the water on light transmission. A speed indicator 13 may be, for example, an anemometer or similar device to measure velocity. Other water quality measurements are performed by sensor 15 for temperature (thermistor, thermometer, or similar instrument), pH, salinity, and/or dissolved oxygen.

The signals 17, 19, 21, 23, 25, 27, 29, respectively, from the above measuring devices, go through a signal conditioning stage 31 having, for example, filters, pre-amplifiers, and amplifiers. The conditioned signals 33 are converted from analog to digital signals by a data acquisition system 35. The converted signals 37 are sent to a processor 39 where they are processed through algorithms using, for example, a digital signal processor (DSP), integrated circuit, field programmable gate array (FPGA), embedded system, or other similar device. The algorithms calculate the light attenuation through the water to the surface based on the light levels, depth, water-quality characteristics, and/or all other parameters input from the signals. Batteries or external power source 41 supplies power 43 to the devices, electronics and instruments. The output 45 of the processor 39 algorithms may be shown on a display 47 and/or output to a computing device, for example, computer or other device 51 via USB, serial, or similar interface 49.

FIG. 2 shows details of the flow-through detector apparatus 50. A flow agitator 53 at the inlet 55 of the tube 57, includes adjustable turning vanes, grating or similar device 59, which induces turbulence and flow excitation that stimulates bioluminescent activity within the tube 57+. The magnitude of flow excitation scales correspondingly as the movement speed of the craft/swimmer. Sensors 61 mounted in/on the inside surface 63 of the tube 57 measure the bioluminescence intensity in the absence of ambient external illumination. The turning vanes 59 can be adjusted by a device 64 on the tube 57, to increase flow excitation 65 and provide predictive measurements by sensors 61 inside tube 57 of bioluminescence (i.e., light levels that would be present if the craft/swimmer changed movement speed).

FIGS. 3A and 3B show examples of a system implemented onto the tail assembly of a submersible (Seal Delivery Vehicle or SDV). In FIG. 3A the detectors 71 and accessories 69 are installed on the submersible 67 without adversely affecting the hydrodynamics or other features of the submersible, i.e., the mounting of the inventive device is non-intrusive to the purpose of the user, whether it is a swimmer, diver, submersible or any other underwater object. Detectors 71 may include any one or more of those shown or described with reference to FIG. 1 and accessories may include any one or more of those shown or described with reference to FIG. 1 (for example, batteries, circuitry, transmissometer, depth gauge, other sensors, etc.). FIG. 3B is a detail of the device shown in FIG. 3A. Detectors 71 and accessories 69 include ambient light detector 73, primary detector 75, photodiodes 77 with fields of regard 79, all part of the device mounted on the submersible 67. These provide the real-time continuous feedback to the operator/user of the device and allow for continuous adjustment of movement, speed, position, and other characteristics desired by the user.

FIG. 4 shows a conceptual rendering of the sensor system 81, with the detector system 71 and accessories 69, mounted on a submersible 83.

The technology includes, but is not limited to, the following advantageous characteristics:

1. Low power: the sensor can be battery powered at low levels or powered by an external source.

2. Low profile: the system has small form factor. The detector and accessories are compact and have little or no impact on craft hydrodynamics, maneuverability, and additional bioluminescence generation (FIGS. 3A, 3B).

3. Simple: the system is low-cost, easy to install and remove, and does not have any negative impact on operator workflow or efficiency (FIGS. 1-4).

4. Real time: the system provides continuous, instantaneous bioluminescence signature information for self-monitoring of detection vulnerability.

5. Multi-sensor configuration: the primary sensor, or sensors, directly measure bioluminescence intensity (photons/time) in the wake of the submersible. Nominally mounted at or near the tail/rudder assembly of the craft, each sensor has collection optics and a photodiode, photomultiplier, or other photodetector. One or more additional sensors may be oriented away from the primary detector to measure ambient illumination conditions. Analog circuitry, batteries and other sensors may be placed in a hydrodynamically benign location.

6. Internal flow-through apparatus: a cylindrical volume with an adjustable flow agitator such as turning vanes or grating excites bioluminescent activity within the enclosed volume. Photosensors inside the volume measure bioluminescence intensity due to flow excitation, which scales as the speed of movement, as shown in FIG. 2.

7. Sensor size/shape: miniature components and hydrodynamic shaping are used to minimize any effects the sensor will have on craft hydrodynamics and maneuverability.

8. Signal-to-noise ratio (SNR): using a multi-sensor design, the measured wake bioluminescence intensity is compared with ambient-light measurements to determine the net effect of craft/propeller-induced illumination (FIG. 4). Information provided by the ambient-light sensor(s) are used in vulnerability assessment. High ambient light levels decrease bioluminescence SNR, reducing surface signature.

9. Other water-quality sensors: a compact beam transmissometer, or other similar turbidity meter, can be used to measure water turbidity and light attenuation, and a digital depth gauge is used to measure depth. Other water-quality parameters (including pH, salinity, temperature) can be measured, as shown in FIG. 1. Resulting data is used to determine a surface signature of bioluminescence illumination based on radiative transfer from depth to the surface through a turbid medium.

10. Display: an indicator of bioluminescence signature ranging from simple (red/yellow/green condition) to detailed (numerical readings of measured parameters and surface signature) based on light intensity, SNR, water quality and depth. When coupled to a craft hydrodynamic model, the display could specify maximum speed, minimum depth and other tactics to achieve acceptable maximum surface signature. Output can also be in digital form, interfaced to a computer or other instrument.

While the invention has been described with reference to specific embodiments, modifications and variations of the invention may be constructed without departing from the scope of the invention.

We claim:

1. A device comprising:
an in-situ bioluminescence sensor disposed on a surface of an object submerged underwater, wherein the sensor comprises a first set of one or more photodetector directed towards the wake of said object, a second set of one or more photodetectors directed towards the ambient light, one or more detectors for flowing through ambient water therethrough and for in-situ measuring of flowed-through water characteristics in an enclosed space of the sensor, a depth gauge, a measurement device to measure ambient water characteristics, a speed indicator for indicating speed of the object, a temperature measurement device, a pH measurement device, a salinity measurement device, a signal conditioning stage, a data acquisition system, a processor programmed to compare the intensity of the bioluminescence found in the wake of the object as detected by the first photodetectors to the ambient conditions as detected by the second photodetectors and to calculate the relative visibility of the object to an observer at the surface and report that information to the operator by way of an output in real-time including bioluminescence signature caused by the wake of the object in water, and a power source.

2. The device of claim 1, further comprising a dissolved oxygen measurement device.

3. The device of claim 1, wherein the photodetectors are selected from the group consisting of photodiodes, avalanche photodiodes (APD), photomultipliers, balanced photoreceivers, spectrometers, channel multiplier tubes or similar photodetectors.

4. The device of claim 1, wherein the device to measure turbidity is selected from the group of light transmissometers, turbidity meters, or similar devices to determine the effect or suspended solids in the water on light transmission.

5. The device of claim 1, wherein the speed indicator is an anemometer or other similar device to measure velocity.

6. The device of claim 1, wherein the temperature measurement device is selected from the group consisting of thermistors, thermometers, or other similar instruments.

7. The device of claim 1, wherein the power source is an external power source.

8. The device of claim 1, wherein the power source is a battery.

9. The device of claim 1, wherein the signal conditioning stage further comprises filters, pre-amplifiers, and amplifiers.

10. The device of claim 1, wherein the processor consists of a DSP, integrated circuit, FPGA, embedded system or other similar device.

11. The device of claim 1, wherein the output system is a display.

12. The device of claim 1, wherein the output system is a computing device.

13. An in-situ bioluminescence detection apparatus comprising an object submerged under water, a first detecting device submerged underwater and positioned on a surface of the object submerged under water, the first detecting device directed towards a wake of the object submerged under water, a second detecting device submerged underwater and positioned on a surface of the object submerged under water, the second detecting device directed towards water unaffected by the submerged object, sensors for measuring bioluminescent activity in the wake of the water, a data acquisition system communicating with the detecting devices, a processor communicating with the detecting devices and programmed to calculate the relative intensity of the bioluminescence caused by the object relative to ambient conditions by comparing the output of the first detecting device with the output of the second detecting device, an output in real-time from the processor indicating detected properties of the water, and a display including bioluminescence signature data display caused by the wake of the object in the water, thereby providing information to the operator of the object about the visibility of the object to an observer on the surface.

14. The apparatus of claim 13, wherein the detecting device further comprises devices selected from the group consisting of photodetectors, ambient light detectors, depth gauges, water characteristics measurement devices, speed indicators, temperature measurement devices, pH measurement devices, salinity measurement devices, dissolved oxygen measurement devices, and combinations thereof.

15. The apparatus of claim 14, wherein the photodetectors are selected from the group consisting of photodiodes, avalanche photodiodes, photomultipliers, balanced photoreceivers, spectrometers, channel multiplier tubes, and combinations thereof.

16. The apparatus of claim 13, further comprising turbidity measurement devices for determining light transmission effects on solids suspended in the water selected from the group consisting of light transmissometers, turbidity meters, and combinations thereof.

17. The apparatus of claim 14, wherein the temperature measurement device is selected from the group consisting of thermistors, thermometers, and combinations thereof.

18. The device of claim 14, wherein the speed indicator is an anemometer or a device to measure velocity.

19. The apparatus of claim 13, further comprising a power source selected from the group consisting of an external power source or a battery.

20. The apparatus of claim 13, further comprising a signal conditioner selected from the group consisting of filters, pre-amplifiers, amplifiers, and combinations thereof.

21. The apparatus of claim 13, wherein the processor is selected from the group consisting of DSPs, integrated circuits, FPGAs, embedded systems and combinations thereof.

22. The apparatus of claim 13, wherein the detecting device comprises at least one detector including an inlet and an outlet for flowing the water therethough, a space between the inlet and the outlet for the flowing water, further comprising a flow agitator proximal the inlet of the detecting device for agitating the water flowing through the detection device.

23. The apparatus of claim 22, wherein the flow agitator comprises flow excitation devices for stimulating bioluminescent activity in the water flowing therethrough.

* * * * *